United States Patent [19]

Klockner et al.

[11] Patent Number: 5,126,473
[45] Date of Patent: Jun. 30, 1992

[54] PROCESS FOR THE HYDRIDING OF HALOGEN-SUBSTITUTED COMPOUNDS

[75] Inventors: Hans-Juergen Klockner, Hanau; Ralf Schmoll, Mainz; Peter Panster, Rodenbach; Peter Kleinschmit, Hanau, all of Fed. Rep. of Germany

[73] Assignee: Degussa Aktiengesellschaft, Frankfurt am Main, Fed. Rep. of Germany

[21] Appl. No.: 565,433

[22] Filed: Aug. 10, 1990

[30] Foreign Application Priority Data

Aug. 11, 1989 [DE] Fed. Rep. of Germany ....... 3926595

[51] Int. Cl.⁵ .................... C07F 7/02; C07F 5/02; C07F 9/02
[52] U.S. Cl. ........................ 556/473; 556/7; 556/8; 556/9; 556/13; 556/64; 556/81; 556/70; 556/87; 556/95; 556/104; 556/487; 556/489; 568/1; 568/16; 568/17
[58] Field of Search ............ 556/7, 8, 9, 13, 64, 556/81, 70, 87, 95, 104, 472, 487, 489; 568/1, 16, 17

[56] References Cited

FOREIGN PATENT DOCUMENTS 1080077 4/1986 Fed. Rep. of Germany.

OTHER PUBLICATIONS

Grant, J., *Hackh's Chemical Dictionary*, 4th Ed., McGraw-Hill Book Co., N.Y., pp. 329-330, 1972.
Inorganic Chemistry, vol. II, pp. 43-46, (1963).
Z. Chem. vol. 23, 1983, p. 349.
Agnew. Chem., vol. 70, 1958, p. 625-627.

*Primary Examiner*—Jose G. Dees
*Assistant Examiner*—Porfirio Nazario
*Attorney, Agent, or Firm*—Beveridge, DeGrandi & Wellacher

[57] ABSTRACT

A process is described for the hydrided of halogen-substituted compounds of the second to fourth period of Groups III to V of the periodic system, with the exception of gallium, aluminum, carbon, or nitrogen. A finely-granulated aluminum is added to a molten salt melt that consists of 50-67 molar % $AlCl_3$ (anhydrous) and 50 to 33 molar % of sodium chloride. Then to the stirred, or by some other means dispersed suspension, hydrogen is introduced to hydrided the finely-dispersed aluminum. Thereafter the mixture is reacted with the halogen-substituted compound and the resulting hydrided compound is renewed.

4 Claims, No Drawings

PROCESS FOR THE HYDRIDING OF HALOGEN-SUBSTITUTED COMPOUNDS

INTRODUCTION AND BACKGROUND

The present invention relates to a process for hydriding halogen-substituted compounds of elements of the 2nd to 4th period of Groups III and V of the periodic table of elements with the exception of gallium, carbon, aluminum, and nitrogen.

For the synthesis of covalent hydrides of the elements silicon, germanium, and boron, the reaction of the corresponding halides with the ionic hydrides of the alkali metal and alkaline earth metals in molten salt has been described in the past. See German Patent 10 80 077; W. Sundermeyer, O. Glemser, Angew. Chemie 70 (1958) 625; H.-H. Emons et al., Z. Chem. 23 (1983) 349.

In selecting the components for the formation of the molten salt bath, care must be taken that the melt is not reduced as a result of reaction with the hydrides of the alkali metal and alkaline earth metals. Furthermore, the temperatures used in carrying out the reaction have an upper limit as a result of the incipient thermal decomposition of the hydrides of boron, silicon, and germanium. Thus, thermal decomposition begins at 400° C. in the case of silane, and, in the case of germanium, 280° C.

If, under these constraints, consideration is given to the possible combinations of salts, whose components are stable in the presence of alkali metal and alkaline earth metal hydrides, and whose eutectic is at a maximum of 350° C., it is apparent that only mixtures of salts that contain lithium chloride meet these criteria.

However, the use of a molten salt melt containing LiCl has a significant disadvantage. In the course of the reaction of the alkali metal or alkaline earth metal hydride with the halides of silicon, germanium, boron, etc. to form the corresponding hydrogen compounds and with the simultaneous formation of the halides of the alkali metal or alkaline earth metals, the composition of the molten melt changes. Therefore, extra addition of individual components of the melt is necessary in order to keep the composition of the melt constant. This leads to a corresponding increase in the volume of the melt so that, in order to avoid overfilling the reactor a portion of the melt must be drained off. The draining can take place either constantly or at intervals.

The LiCl which appears in the waste sediment has a high value and therefore necessitates expensive processing for recovery.

H. L. Jackson et al. (Inorg. Chem. 2 (1963) 43) describe a process in which silicon tetrachloride and dimethyldichlorosilane are caused to react with hydrogen to form silane in a NaCl-AlCl$_3$ eutectic melt in the presence of aluminum under extremely high pressures (several hundred bars) and with long reaction times. Details pertaining to yields are not included in this publication, but it is said that as a result of using dimethyldichlorosilane only low conversion is achieved.

The aim of the invention is to provide a process by means of which it is possible to hydride halogen-substituted compounds of various elements with high yields in molten salt melts that contain no lithium chloride.

SUMMARY OF THE INVENTION

An object of the invention is to provide a process of hydriding halogen-substituted compounds of elements of the second to fourth period of Groups III to V of the periodic system with the exception of gallium, aluminum, carbon, nitrogen.

In carrying out the invention there is provided a process comprising:

a) adding finely granulated aluminum to a molten salt melt including 50 to 67 molar % AlCl$_3$ (anhydrous) and 50 to 33 molar % sodium chloride, b) introducing hydrogen with stirring or with other means of agitation, to form a suspension of dispersed aluminum in order to hydride the finely dispersed aluminum, c) then causing the resultant mixture to react with the halogen-substituted compound, and d) isolating the hydrided compound.

The reaction proceeds according to the following equation (for instance, using SiCl$_4$):

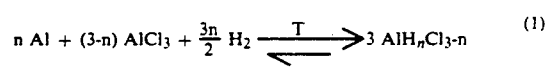

Total Balance: (3)

The proper ratios of concentrations of sodium chloride and AlCl$_3$ in the melt are prescribed by the phase diagram of the system as will be understood by those familiar therewith.

If the mixture contains more than 50 molar % of sodium chloride, then this component is present in the melt in suspended solid form.

If AlCl$_3$ is present in the melt in a quantity of more than 67 molar % potential problems could arise as a result of this compound's tendency toward sublimation. In spite of this however, the overall process remains feasible.

The aluminum powder, which is initially present in the form of a suspension reacts with hydrogen in accordance with equation (1).

The desired degree of hydriding of the compounds according to formula (1) is generally not disturbed by the presence of an excess of the suspended aluminum powder.

Since the total balance in accordance with equation (3) in the course of the reaction, additional AlCl$_3$ is formed, extra NaCl must be added to maintain the desired NaCl/AlCl$_3$ molar ratio.

Surprisingly, the process takes place with a high degree of conversion under normal pressure conditions.

It is also possible to carry out a reaction yielding the desired end product at elevated pressures, but it involves considerably greater expenditure due to the pressurizing apparatus that then becomes necessary.

The particle size of the aluminum that is added to the AlCl$_3$ melt is not critical. Preference is given to a finely-granular powder with a distribution of granules ranging from 32 to 150 μm.

Preferably, aluminum is used that contains 0.03 to 0.25% by weight, particularly 0.1 to 0.2% of at least one hydrogen-transferring metal with reference to the aluminum. Titanium, zirconium, hafnium, vanadium, niobium, nor nickel are illustrative; and titanium is preferred. Aluminum that was atomized under inert gas proves to be particularly efficacious. Aluminum powder that was obtained as a result of melt-flow electrolysis may be used.

The introduction of the hydrogen into the AlCl$_3$-NaCl melt preferably occurs until no further hydrogen is absorbed, or, until the added aluminum powder is substantially dissolved.

If the aluminum is not alloyed with a hydrogen-transferring metal, then a hydride, particularly NaH, TiH$_2$, or LiAlH$_4$, is added to the melt, preferably 0.1 to 0.5% by weight, based on the quantity of aluminum, before adding the hydrogen (Step (b)).

In general, an amount of aluminum is added to the melt sufficient for the hydrating compound, AlH$_n$Cl$_{3-n}$' to contain a content of 0.01 to 10 molar % based on the molar total of AlCl$_3$ and NaCl.

In accordance with the process of the invention, a large number of halogen-substituted compounds can be hydrided.

In the total balance, as shown by equation (3), at least 0.5 moles of hydrogen (H$_2$), and 0.33 moles aluminum are converted through the hydriding of the halogen atom to be split off.

Halogen-substituted compounds having the general formula

  (1)

R is Methyl, phenyl,
X is Chlorine, fluorine, preferably chlorine;
a+b+c=e whereby c is at least 1, and c and e are no more than 4 (in the case when M is B, P, or As, e is at most 3); a and b form the balance, and M is in general B, Si, Ge, P, As, preferably Si.

A prerequisite of all reactions of this kind is that the products be thermally resistant to the temperatures that are used in the process and that they escape from the melt in gaseous form.

The exchange of one or more halogen atoms for hydrogen atoms may occur, thus, for example, in the case of the halogensilane of the series SiHX$_3$, SiH$_2$X$_2$, and SiH$_3$X, particularly where X=chlorine.

When BX$_3$ is used, B$_2$H$_6$ is formed, whereas, in all other hydrides no dimers are formed.

The temperature of the melt lies within the range of 130° C. to 300° C., preferably 152° C. to 225° C.

The preferred reaction temperatures of the hydriding of aluminum powder, as well as for the reaction of the hydriding agent, is obtained in this way with the halogen-substituted compound also lie within this range. To the extent that the compounds to be hydrided are present in gaseous form, they are introduced in conjunction with a carrier gas, such as H$_2$, N$_2$, or Ar in a mixture of 1 to 99% by volume to the reaction melt, which contains the hydriding agent.

At the same time, the rate of flow is governed by the rate of the reaction.

The halides may also be added in liquid or solid form.

The mixtures of gases that leaves the melt is conveyed through cooling stages according to well-known techniques, and the hydrided product is separated out in this manner.

Compounds that did not take part in the reaction and the hydrogen can then be led back to the melt.

If the process is performed on a continuous basis, steps a) and b) are performed in a separate reactor vessel; the pre-mixture that is obtained in this case is conveyed to the actual reaction boiler. Subsequently, the AlCl$_3$ that is formed in the reaction where the NaCl was added to form NaAlCl$_4$, is continually drawn off.

It is possible to recover the aluminum powder from the separated NaAlCl$_4$ by means of melt-flow electrolysis as in equation (4), and in this way to conduct a cyclical process in accordance with the empirical formula (5):

Electrolysis  (4)

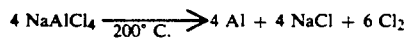

  (5)

If a porous cathode is used in the electrolysis of the NaAlCl$_4$ melt, through which hydrogen is pressurized into a melt, the separated aluminum can be converted into the complex aluminum-hydrogen compound that dissolves in the melt.

DETAILED EMBODIMENT OF THE INVENTION

EXAMPLES

EXAMPLE 1

In a 4-liter mixing reactor, 7.8 moles of anhydrous aluminum chloride and 7.8 moles of sodium chloride are weighed in, to the exclusion of all moisture and melted at 200° C. One mole of aluminum powder is added to this melt (Type ECKA Al grit, particle size <63 μm, Fe 0.2–0.34%, Si 0.05–0.14%, Zn 0.01%, Ti 0.15–0.02%, balance: Al), and suspended following thorough mixing.

For a period of 2 hours, at atmospheric pressure and a temperature of 200° C., hydrogen is introduced to the stirred suspension of aluminum powder in the NaAlCl$_4$ melt, at a rate of flow of approximately 30 l/h:

Then, while simultaneously introducing hydrogen gas into the melt, SiCl$_4$ is introduced to the melt. Within 1.5 hours reaction time, 7.5 g SiCl$_4$ (0.44 mole) were converted.

Following separation of the unconverted SiCl$_4$ at −78° C., 1.0 g of SiH$_4$ (0.031 moles) is obtained at −196° C. (Yield: 70%)

EXAMPLE 2

Under the same conditions as in Example 1, (CH$_3$)$_2$SiCl$_2$ is introduced into the NaAlCl$_4$ melt, which contains the hydriding agent. Within 1.5 hours reaction time, 16.3 g (CH$_3$)$_2$SiCl$_2$ (0.126 moles) are converted.

Following the separation of the unconverted (CH$_3$)$_2$SiCl$_2$ at 0° C., 6.4 g (CH$_3$)$_2$SiH$_2$ (0.107 moles) are obtained at −78° C. (Yield: 85%).

EXAMPLE 3

Under the same conditions as those of Example 1, AsCl$_3$ is led into the NaAlCl$_4$ melt, which contains the hydriding agent. Within 1.5 hours reaction time, 21.75 G AsCl$_3$ (0.12 moles) are converted.

After separation of the AsCl$_3$ at 0° C., 4.7 G AsH$_3$ (0.06 moles) are obtained. (Yield: 50%).

Further variations and modifications of the foregoing will be apparent to those skilled in the art and are intended to be encompassed by the claims appended hereto.

We claim:

1. A process for hydriding halogen-substituted compounds of elements of the second to fourth period of Groups III through V of the periodic system with the exception of gallium, aluminum, carbon, nitrogen, comprising:
   a) adding finely particulate aluminum to a molten salt melt, comprising of 50 to 67 molar % $AlCl_3$ (anhydrous) and 50 to 33 molar % sodium chloride, wherein said aluminum contains 0.03 to 0.25% by weight of at least one hydrogen-transferring metal,
   b) introducing hydrogen into the melt with agitation to form a dispersion and thereby to hydride the finely dispersed aluminum,
   c) reacting the resultant mixture with a halogen-substituted compound, to form a hydrided compound, and
   d) isolating the hydrided compound.

2. A processing according to claim 1, wherein said metal is titanium, zirconium, hafnium, vanadium, niobium, or nickel.

3. A process according to claim 1, further comprising adding 0.1 to 0.5% by weight of a hydride based on the amount of aluminum prior to step b).

4. The process according to claim 1, wherein the aluminum is in the form of granules ranging in size from 32 to 150 μm.

* * * * *